United States Patent [19]

Oxford et al.

[11] Patent Number: 5,162,112

[45] Date of Patent: Nov. 10, 1992

[54] INFLUENZA VACCINE

[75] Inventors: John S. Oxford, London; James S. Robertson, St. Albans; Geoffrey C. Schild, London; David A. Tyrrell, Salisbury, all of England

[73] Assignee: National Research Development Corporation, London, England

[21] Appl. No.: 506,533

[22] Filed: Apr. 9, 1990

Related U.S. Application Data

[63] Continuation of Ser. No. 156,035, Feb. 16, 1988, abandoned.

[30] Foreign Application Priority Data

Feb. 18, 1987 [GB] United Kingdom ................ 8703696

[51] Int. Cl.$^5$ .................... A61K 39/12; C12N 7/00; C12N 7/04; C12N 7/08; C12N 7/06; C12N 7/02; C12Q 1/70; C12Q 1/68

[52] U.S. Cl. ................................. 424/89; 435/235.1; 435/236; 435/237; 435/238; 435/239; 435/5; 435/6; 435/7.2; 435/7.21

[58] Field of Search ............... 424/89; 425/235.1, 236, 425/237, 238, 239, 5, 6, 7.2, 7.21, 7.25; 436/520

[56] References Cited

U.S. PATENT DOCUMENTS 4,040,905  9/1977  Petricciani .................. 435/235 X

OTHER PUBLICATIONS

Oxford et al., (1986) Abstract only Vaccine 4(1), 9–14.
Katz et al., (1987 Feb.) Virology 156; 386–395.
Katz et al., (1988 Aug.) Virology 165: 446–456.
G. C. Schild et al., Nature 303, 706–709 (1983).
G. S. Schild et al. in "The Molecular Virology and Epidemology of Influenza", ed. Sir C. H. Stuart-Harris and C. W. Potter, pp. 163–174, Academic Press (1984).
G. Winter et al., Nature 292, 72–75 (1981).
M. Krystal et al., Proc. Natl. Acad. Sci. USA 79, 4800–4804 (1982).
F. L. Raymond et al., Virology 148, 275–287 (1986).
J. S. Robertson et al. in "The Biology of Negative Strand Viruses", ed. B. W. J. Mahy and D. Kolakofsky, pp. 412–416, Elsevier Biomedical Press (1987).
J. S. Robertson et al., Virology 143, 166–174 (1985).
J. S. Robertson, oral paper given at the Department of Cellular, Viral & Molecular Biology, University of Utah, Salt Lake City, Apr. 28, 1985.
J. S. Robertson, oral paper given at a symposium by UCLA, Keystone, Co. Apr. 20–25, 1985.
J. L. Lathey et al., Journal of Medical Virology 19, 155–159 (1986).
S. Patterson and J. S. Oxford, Vaccine 4, 79–90 (1986).
J. S. Robertson, oral paper, Wistar Institute, Phila., Sep. 20, 1984.
J. S. Robertson et al., "Modern Approaches to Vaccines", Abstracts of papers presented at the 1984 meeting at the Cold Spring Harbor Laboratory, New York, Sep. 12–16 1984.
J. S. Robertson et al., J. Cellular Biochem., Supplement 9C, Abstract No. 1827, p. 270 (1985).
J. S. Robertson et al., Virus Research Supplement 1, Abstract No. 156, p. 79 (1985).
S. Patterson et al., Archives of Virology 88, 189–202 (1986).
J. S. Robertson et al., in "Vaccines 85", edited by R. A. Lerner, R. M. Channock and F. Brown, Cold Spring Harbor Laboratory, New York (1985), pp.333–337.
D. W. Naeve et al., American Society for Virology, 1984 Annual Meeting. Abstracts, p. 10.
J. S. Robertson et al., Virology, 160, 31–37 (1987).
J. S. Oxford et al., Bulletin of the World Health Organization 65 (2), 181–187 (1987).
M. W. Harmon et al., J. Clinical Microbiology 26, 333–337 (Feb. 1988).
P. A. Rota et al., Virology 161, 269–275 (1987).

Primary Examiner—Christine M. Nucker
Assistant Examiner—David R. Preston
Attorney, Agent, or Firm—Nixon & Vanderhye

[57] ABSTRACT

A strain of influenza virus, especially human influenza type A or B, for use in formulating a vaccine is selected by a process which comprises isolating candidate influenza viruses in embryonated hens' eggs, determining whether they have antigenic similarities to strains which are the same except that they have been isolated and grown exclusively in animal cells, that is to say whether they are "cell-like", and selecting at least one such cell-like strain or a reassortant thereof having its HA and NA genes for the vaccine.

7 Claims, No Drawings

INFLUENZA VACCINE

This is a continuation of application Ser. No. 07/156,035, filed Feb. 16, 1988, now abandoned.

BACKGROUND OF THE INVENTION

1. Field of the invention

This invention relates to a method of selecting a strain of virus use as a component of a vaccine against influenza, to a method of preparing such a vaccine and to the vaccine when prepared by the invented method.

2. Description of prior art

Influenza is still a major disease in man, primarily because of the property of antigenic variation associated with influenza virus. There are three types of influenza viruses (A, B, and C) that are defined by the absence of serologic crossreactivity between their internal proteins. Influenza A viruses are further classified into sub-types based on antigenic differences of their glycoproteins, the haemagglutinin (HA or H) and neuraminidase (NA or N). The most important types of influenza virus in humans currently are type A sub-types H1N1 and H3N2 and type B. These are therefore the types which are incorporated in influenza vaccines.

The haemagglutinin (HA) antigens of influenza viruses A and B undergo frequent and progressive changes in antigenic specificity, whereby the virus seeks to evade neutralisation by the immune response of the human body. This "antigenic drift" results from changes in the amino acid sequence of HA and NA antigens, brought about by natural selection, presumably under pressure of the immune response. It is well known that vaccination with a particular strain of influenza virus, which is isolated from a particular outbreak of influenza, is unlikely to confer complete protection against a future outbreak. New vaccines are, therefore, continually being prepared from recent isolates to counter the latest antigenic drift. With influenza A viruses, this incorporation of new strains in the vaccine is at most a yearly occurrence.

It is the practice in preparing influenza vaccines on a commercial scale to grow an isolated strain in embryonated hens' eggs. Initially the virus is recovered from a throat swab or similar source and isolated in eggs. The initial isolation in eggs is difficult, but the virus adapts to its egg host and subsequent propagation in eggs takes place relatively easily. In contrast, while the initial isolate can usually be made in mammalian tissue culture, using, for example, the well known canine kidney cells known as MDCK, mammalian tissue culture has not been favoured for the large scale production of influenza vaccines, because of fears about possible adverse effects of the use of transformed cells. Such cells are currently not licensed for use as a substrate in vaccine production. Furthermore, there are production problems in the use of alternative cells such as human diploid cells.

Because of antigenic drift of the most important single influenza virus protein, the haemagglutinin (HA), the suitability of current virus strains for vaccines must be continually reassessed. This has been performed for the last 3 decades by analysing the antigenic structure of the HA of field strains isolated and cultivated in embryonated hens' eggs. Usually a number of such candidate virus strains are screened versus polyclonal ferret and human antisera and more recently monoclonal antibodies using the haemagglutination inhibition (HI) test. A virus which reacts poorly and to low frequency with human sera is commonly selected and such a virus (or a reassortant containing the HA and NA genes of the virus) is further passaged in eggs to produce virus in quantities for inactivated vaccine. It has been thought that the criterion of poor reactivity is indicative of a virus which has undergone antigenic drift, and against which the human population would show little resistance. Such a virus could cause a future epidemic and so might be the best choice for use in vaccines.

Doubts about the efficacy of some influenza vaccines have long been expressed by clinicians. These have been given added weight by recent evidence derived from antigenic comparison of egg-adapted virus with virus grown exclusively in mammalian tissue culture. Using both monoclonal and polyclonal antibodies in haemagglutination-inhibition (HI) and virus neutralisation assays. G. C. Schild et al., Nature 303, 706-709 (1983) and in "The Molecular Virology and Epidemiology of Influenza" (Ed. Sir Charles Stuart-Harris and Professor C. W. Potter), Academic Press, London, New York and Orlando, (1984), pages 163-174 have demonstrated that egg-adapted virus is antigenically distinct from virus from the same clinical sample grown solely in tissue culture (MDCK) cells. In addition, MDCK-derived influenza B or A (H1N1) virus detects antibody more frequently and to a higher titre in postinfection human sera using haemagglutination-inhibition and neutralisation tests than does egg-adapted virus. G. C. Schild and his colleagues J. S. Oxford and J. S. Robertson at the National Institute for Biological Standards and Control, Blanche Lane, South Mimms, Potters Bar, Hertford, EN6 3QG, have described these findings as having serious implications in relation to the continued use of egg-adapted viral strains for epidemiological studies, virus research and possibly vaccine production.

The haemagglutinin (HA) antigen provides the major antigenic determinants of influenza virus. Its role is to attach the virus to the host cell and thereafter intracellularly to fuse the envelope of the virus to the cell membrane. The three-dimensional structure of an H3 subtype of HA is established. Antigenic sites for HA of H1N1 and H3N2 and of influenza B have been identified and are located predominantly on the surface of the "globular head" of the protein. The site at which the HA attaches to the cell has also been identified as on the globular head.

The nucleotide and amino acid sequences of many HAs are known. Thus G. Winter et al., Nature 292, 72-75 (1981) have sequenced HA from the H1 sub-type, and compared it with that of the H2 and H3 sub-types of influenza A, while M. Krystal et al., Proc. Natl. Acad. Sci. USA 79, 4800-4804 (1982) have sequenced HA of a type B virus, and F. L. Raymond et al., Virology 148, 275-287 (1986) have analysed the HA nucleotide sequence in the globular head region for 19 strains of type A sub-type H1 isolated from 1950 to 1983. It is customary, in this field, to use an amino acid numbering system based on an H3 sub-type as set forth by G. Winter et al., supra., at page 74. The numbering system allows for deletion and insertion differences in H1, H2 and H3 sub-types of serotype A and is also used for type B. This numbering system is used in this specification, except where otherwise stated.

J. S. Robertson et al., have given several papers in 1984 and 1985 analysing the amino acid difference in HA between strains of virus (a) isolated and grown in cells and (b) isolated in cells and subsequently egg-adapted. The paper given orally at Cambridge, England in September 1985 and entitled "Characterisation of egg-adapted variants of human influenza viruses" is believed representative. This paper has been published in "The Biology of Negative Strand Viruses" (Ed. B. W. J. Mahy and D. Kolakofsky), Elsevier Biomedical Press (1987), pages 412–416. It is reported that a feature common to the HA of all egg-adapted viruses examined is the location of amino acid substitution(s) adjacent to the receptor binding site. In A(H1N1), residues 138, 187, 189, 190 and 225 are all located in the proximity of the receptor binding site. Residue 163 which forms part of a glycosylation site in the HA of cell culture derived H1N1 virus, is located on the opposite side of the molecule from the receptor binding site; however the presence of a carbohydrate side chain on the N (asparagine) residue at 163 might affect the receptor specificity of an adjacent HA molecule. In A(H1N1) some of these changes (residues 163, 190 and in some cases 225) did not appear to alter the antigenicity of the HA whilst others did (residues 187, 189 and in some cases 225), and some (residues 65, 138, 300) occasionally accompanied substitution at 187 and 189 and may have contributed towards the altered antigenicity of these variants. In the B serotype, see also J. S. Robertson et al., Virology 143, 166–174 (1985),. HA residues 196–198 in B type nomenclature (equivalent to 187–189 in H3 numbering) constitute a glycosylation site. Egg adaptation of B type virus is accompanied by an amino acid substitution of either N at 196 or T at 198 and a concomitant change in antigenic profile.

In an oral paper given by Dr. J. S. Robertson at the Department of Cellular, Viral and Molecular Biology, University of Utah, Salt Lake City, USA, 26th Apr., 1985 and at a symposium at Keystone, Colorado, USA organised by the University of California, Los Angeles, USA given in April 1985, the antigenic profiles of virus grown in MDCK cells and then egg-adapted have been compared with an MDCK cell-grown virus in a HI test using a test set of several different monoclonal antibodies and human and ferret polyclonal antisera. Some of the egg-adapted viruses could not be distinguished antigenically from cell-grown virus and were termed "cell-like". Others were found to have a different profile which could not be distinguished from that obtained when the initial isolate was made in eggs. These were termed "egg-like". Yet a third group differed from the others and was generally not very reactive towards any of the antibodies. These were termed "odd". These antigenic changes occurring upon passage of the MDCK cell-isolated virus in eggs were correlated with HA amino acid substitutions. In none of these various prior papers have any conclusions been reached concerning what should be done to make influenza vaccines more effective.

J. L. Lathey et al., Journal of Medical Virology 19, 155–159 (1986) have shown that antigenic extract from cell-grown virus, grown in African green monkey kidney cells, is superior to that from egg-grown virus for diagnosis of the course of an infection of influenza B. These authors noted a change in antigenicity when an egg-grown virus was subsequently passaged in the monkey kidney cells, and put forward the idea that the change in amino acid sequence induced by egg passage might be reversible upon subsequent passage in mammalian cells.

S. Patterson and J. S. Oxford recently reviewed the interactions between viruses and host cells in a paper in Vaccine 4, 79–90 (1986). Table 1 of this paper shows the result of an HI test of three monoclonal antibodies to assess the antigenic differences between viruses having various histories of isolation and passage. After discussing these antigenic differences, they comment on the relevance of their results to vaccines. Noting that the antisera of convalescent influenza sufferers react better with viruses cultivated in cells rather than in eggs, they state (page 81, right-hand column) that they are investigating the potential of influenza vaccines prepared in mammalian cells.

The above-mentioned prior disclosures of Robertson et al. were regarded by the present inventors as of scientific interest, in showing that a virus isolated in animal cells and passaged in eggs might remain "cell-like" in antigenic character. This complemented the earlier finding of Schild et al. in the above-mentioned 1983 paper in Nature that a virus isolated in eggs and passaged in cells remained "egg-like" in antigenic character. It seemed to the inventors that growing viruses in eggs for the production of vaccine strains, according to the conventional method, might alter the antigenic profile characteristic of the virus present in a specimen taken from a patient suffering from influenza. Therefore, it seemed to the inventors, it might be better to isolate and grow vaccine strains in animal cells. Given the worries about the use of transformed cells (see above), one would have to use human diploid cells or some other non-transformed animal cells. Production difficulties would be anticipated with such cells and viruses would only be produced at low titres.

SUMMARY OF THE INVENTION

It has now been found that "cell-like" antigenic characteristics are exhibited by certain strains isolated in eggs and which have never been grown in cells. It has further been found that these "cell-like" egg-isolated viral strains react with antibodies to a high titre and are valuable for the formulation of vaccines. It is thus possible to provide vaccine strains by subjecting egg-isolated candidate strains to tests to determine their antigenic character and to select only those candidate strains which are "cell-like".

Thus, the present invention provides a process of selecting a strain of an influenza virus for use in formulating a killed vaccine, which process comprises isolating candidate influenza viruses in embryonated hens' eggs, determining whether they have antigenic similarities to strains which are the same except that they have been isolated and grown exclusively in animal cells, that is to say whether they are "cell-like", and selecting for the vaccine at least one such cell-like strain or a reassortant thereof having its HA and NA genes.

The invention extends to all types of human influenza virus, including especially the very prevalent A(H1N1) sub-type, the A(H3N2) sub-type and the less common B type, and also the influenza viruses which infect other mammals especially horses and pigs and also birds.

Antigenic characteristics can be analysed in any conventional way, preferably using a panel of monoclonal antibodies and/or of polyclonal sera of appropriate animals such as ferrets or humans. It is desirable to make isolates of each candidate strain in eggs and separately in animal cells, for example canine kidney cells, to grow them exclusively in eggs and animal cells respectively, and then to compare the antigenic profiles of those egg-isolated egg-grown and cell-isolated cell-grown strains derived from the same source or specimen. Such a practice provides a good means of "internal reference" to verify that antibodies which react strongly with the cell-like egg-grown strains are also those which react strongly with the corresponding cell-grown strain, i.e. the cell grown strain derived from the same original source or specimen.

Also, many of the egg-grown strains will be egg-like in character, whereby it can be shown that antibodies which react strongly with cell-like egg-grown strains react poorly with egg-like egg-grown strains and the converse. Such reference egg-grown strains need not be isolated in eggs provided that they are successfully passaged in eggs.

The invention further provides a process of preparing a "killed" (inactivated) vaccine, which comprises selecting a viral strain by the invented method and then inactivating the viral particles, for example with the aid of formaldehyde. It also includes a process of preparing a live vaccine which comprises selecting a viral strain by the invented method and attenuating it, preferably by preparing a reassortant thereof having the HA and NA genes of the selected strain.

DESCRIPTION OF THE PREFERRED EMBODIMENTS

When an outbreak of influenza occurs, the local public health laboratory takes samples and if necessary stores them at minus 70° C. They are then sent to a specialist laboratory to check whether a novel vaccine needs to be prepared. i.e. to assess the degree of antigenic drift which has taken place since the last vaccine strains were made. The sample from the recent outbreak is isolated in eggs and preferably also in animal cells as explained above. The animal cells are those of a stable cell line amenable to tissue culture, for example the popular MDCK cells commercially available.

In order to propagate sufficient quantities of the virus further passaging in eggs might be required. It is, however, unwise to passage a candidate virus excessively, e.g. more than about 12 times, in eggs, since it is liable to become altered. For example, where a candidate virus is cell-like it might lose this character if passaged more than about 12 times in eggs. Obviously, the selected candidate strain should not be further passaged in cells. In other words, any growth of the selected strain after the initial isolation must be in eggs. The same applies to the preparation of reassortants.

The egg-grown egg-isolated candidate strains and preferably also their cell-grown counterparts and optionally also egg-grown egg-like reference strains are then conveniently subjected to a haemagglutinin inhibition test, in which the virus is mixed firstly with antibodies and then red blood cells are added. If the virus interacts well with the antibodies, it becomes blocked from taking part in agglutination. Consequently a low degree of agglutination (in practice represented by a fixed degree of agglutination at a high dilution of the virus) signifies that the virus reacts very well with antisera. Other things being equal, a high reaction with human sera suggests that the virus will have potential for use as a vaccine.

To determine whether a given candidate is cell-like in character, it is necessary to use a sufficiently large panel of antibodies. The choice of antibodies is a matter of experience and trial and error. In one preferred embodiment monoclonal antibodies are used. Normally the antibodies are best derived from a strain of the same source or outbreak or from another recent outbreak within the same region of population mobility. Out-of-date strains sometimes provide useful antibodies but are less reliable. It is for this reason that the present applicants have not deposited any hybridoma cell lines: within a few years, when it is hoped that patents will issue, so much antigenic drift of influenza viruses will have taken place that the chances of the monoclonal antibodies secreted by such present day hybridomas being useful in relation to an outbreak of influenza at that future time are not high.

Hybridomas secreting monoclonal antibodies for use in the present invention can be prepared from mouse myelomas and mouse spleen cells by the conventional method. Thus, mice were inoculated intraperitoneally with 100 micrograms of influenza viral protein. Booster inoculations of the same protein were given 6 and 10 weeks from the first inoculation. Three days later the spleens were removed and used in the fusion in the conventional way.

It is also possible to use polyclonal antisera from any immunologically competent influenza-susceptible animal e.g. from ferrets or humans, as the antisera for testing the candidate strains. The ferret exhibits visible symptoms of influenza in a short time after infection, typically about 3 days. Thus, ferrets can be infected with a novel isolate, e.g. intranasally and then antisera obtained very soon after identification of an outbreak of influenza. With experience, it is expected that it will not be necessary to use more than 4 ferrets, 2 infected with the cell isolate and 2 with the egg isolate of the same parental viral strain.

The differences between cell-like and egg-like egg-grown viruses may be seen from immune responses either post infection or post immunisation in ferrets, hamsters and guinea pigs and preliminary indications are that human immune responses also differentiate them.

While the invention will in the first instance be applicable to selecting a strain suitable for use in formulating a vaccine (herein called a vaccine strain) from wild strain candidates, the same technique is applicable to analysing reassortants made from a candidate vaccine virus. Virus reassortants are obtained by genetic mixing events when two different viral strains (X and Y) are co-cultured, whereby virus X acquires some genes from virus Y and virus Y some from virus X. It is useful to prepare reassortants in order to combine a high growth gene or genes from influenza virus X with the haemagglutinin and neuraminidase genes from the desired cell-like egg-grown virus Y, thereby to improve the growth of the haemagglutinin and neuraminidase genes of virus Y. Any of the well known methods of preparing reassortants can be used. It is preferable to use as parental strain "X" (high growth) in the process one which has the different HA and NA genes, e.g. from type A viruses H3 and N2, whereby the high growth reassortants can be distinguished by their having the HA and NA genes of parental strain "Y" (cell-like, egg-grown), e.g. for type A viruses H1 and N1.

While in the foregoing description emphasis has been laid on determining the antigenic profile by immunological methods, this is not the only way. It is possible to distinguish cell-like egg-grown from egg-like viruses in terms of the RNA or amino acid sequence of the HA gene. For example, in A(H1N1) viruses cell-like egg-grown and egg-like egg-grown viruses from the same source differ from MDCK grown viruses in their amino acid sequence at residue 163, 187, 189, 190 or 225. Any one of the following changes in egg-grown viruses is associated with cell-like antigenicity: loss of the asparagine residue at 163, a change at 190 to asparagine and a change at 225 to asparagine or glycine. It is therefore possible, by RNA sequencing techniques, to establish or confirm the requisite antigenic differences of cell-like and egg-like viruses by this method. The use of sequence changes to determine antigenic differences between cell-like and egg-like viruses is primarily of interest where a direct comparison is being made between viruses derived from the same original specimen, but it will have some applicability to viruses derived from different specimens but otherwise apparently similar. It is also confidently expected that it will be possible to raise monoclonal antibodies specific to antigenic determinants in these regions of the genes, whereby distinction will be possible on the basis of interaction with a small number of monoclonal antibodies.

The eggs used for isolating and growing viruses will almost invariably be embryonated hens' eggs. The viruses will grow in the amniotic or allantoic cavity. The eggs of other fowl are less useful. It is advisable always to use specific pathogen-free eggs.

For formulating the vaccine any of the conventional methods in influenza technology can be used. The virus component could be formulated as whole virus particles, inactivated for example by formalin or beta-propiolactone, or as a "split" vaccine containing disrupted virions, the disruption being conveniently carried out by the action of detergent. A third possibility is to make a true sub-unit viral component from purified haemagglutinin and neuraminidase extracted from the viral particles. When preparing a split or sub-unit vaccine, the viral particles are normally first inactivated. One useful method of making a sub-unit vaccine is that described by M. I. Brady and I. G. S. Furminger, Journal of Hygiene 77, 161-172 (1976).

A killed vaccine is desirably formulated without an adjuvant in any appropriate sterile medium such as phosphate-buffered saline, preferably containing a preservative. However it is formulated, the potency of the vaccine is normally measured in terms of equivalents of haemagglutinin as measured by the well-known Single Radial Diffusion method. A typical dose for intramuscular adminstration of an inactivated or "killed" vaccine would have a volume of 0.5 ml and contain 10 micrograms of HA. The suggested range of doses for the purposes of the present invention is the same as in current usage. It varies according to the strain and is typically in the range 10 to 20 micrograms of HA/0.5 ml.

A live vaccine can be made as a reassortant of an attenuated strain, e.g. a temperature- sensitive or cold-adapted strain, together with HA and NA genes of the cell-like egg-grown strain selected by the invention. It may also contain conventional additives such as buffers or stabilisers against degradation. A live vaccine is preferably administered intranasally.

The following Examples illustrate the invention.

EXAMPLE 1

This Example shows that when an egg-grown A(H1N1) viral strain having cell-like antigenic characteristics was administered to either guinea pigs or ferrets as a killed vaccine, an immune response comparable to the corresponding cell-grown strain (corresponding in the sense of being derived from the same throat swab) was produced.

The influenza virus strains in this Example are all derived from a throat swab taken from a boy at Christ's Hospital School. Horsham, Sussex, England in 1983 and are of the type A(H1N1). The strain is called A/Christ/157/83. A first isolate thereof made in MDCK cells and passaged once in MDCK cells, is referred to herein for brevity as "157M". A second isolate, from the original swab, was made in the allantoic cavity of embryonated hens' eggs and passaged once in the allantoic cavity and is referred to herein for brevity as "157E". This isolate has an egg-like antigenic profile which differs from that of the cell-grown virus 157M. A third isolate was made by taking virus from the A/Christ/157/83 throat swab, isolating it in the amniotic cavity of embryonated hens' eggs and passaging it once in the allantoic cavity. This isolate, made separately from 157E, has been determined to have a cell-like antigenic profile; that is to say it reacts with antisera similarly to the "157M" and dissimilarly to the "157E". It was designated "157G".

Hereinafter the history of passage isolation is represented parenthetically by the symbols "M", "Al" and "Am" representing MDCK cells and the allantoic and amniotic cavities of embryonated hens' eggs. The numbers indicated refer to isolation and subsequent passage, in accordance with the following illustration:

| Designation | Type | Growth and passage history |
| --- | --- | --- |
| 157M(M$_2$) | Cell-like, cell grown | Isolated in MDCK cells, then passaged once in MDCK cells. |
| 157E(Al$_2$) | Egg-like, egg-grown | Isolated in allantoic cavity of eggs, then passaged once in allantoic cavity of eggs. |
| 157G(Am$_1$Al$_1$) | Cell-like, egg-grown | Isolated in amniotic cavity of eggs, then passaged once in allantoic cavity of eggs. |

The HA RNA of 157M, 157E and 157G was sequenced. The amino acid sequence between residues 147 and 226 is shown below for 157M together with the substitutions by which 157E and 157G differ from 157M:

```
         150       160       170       180       190
157M  FYRNLLWLTEKNGSYPNLSKSYVNNKEKEVLVLWGVHHPSNIED
157E                  S                          K
157G                  N                          E
                200       210       220
157M  QKTIYRKENAYVSVVSSHYNRRFTPEIAKRPKVRDQ
157E                                   D
```

-continued

| | |
|---|---|
| 157G | G |

Tests on guinea pigs

Guinea pigs are immunologically responsive to small quantities of influenza virus equivalent to as little as 2 micrograms of HA. In these experiments twelve animals, in three groups of four, were immunised intramuscularly with vaccine in an amount equivalent to 8 micrograms of HA and boosted 10 days later with vaccine in an amount equivalent to 2 micrograms of HA. The vaccine was made from purified whole virus particles of 157M, 157E or 157G (further passaged as detailed below), as follows. The purified vaccine was concentrated and purified by differential centrifugation in three stages (i) pelleting from bulk fluids (54,000 g at r-max for 90 mins in a Beckman T19 rotor), (ii) rate zonal sedimentation through sucrose gradients (10–40% w/v sucrose in phosphate-buffered saline (PBS) 'A', 90,000 g at r-max for 60 mins in a Beckman SW28 rotor), (iii) removal of virus from sucrose (100,000 g at r-max for 90 mins in a Beckman T35 rotor). This was followed by a final resuspension in PBS 'A' to a concentration of 10 mg/ml (as measured by protein assay). The concentrate was stored in individual vials at $-70°$ C. and inactivated by mixing it in PBS with 0.008% formaldehyde at a final concentration of 0.015% (v/v) and incubating the mixture for 48 hours at $4°$ C. in the dark. Vaccine was found to be free of live virus by inoculation of embryonated hens eggs and MDCK cells.

The HA concentration of the vaccine was measured by the single-radial-diffusion (SRD) test as described by J. M. Wood et al., J. Biol. Standards 5, 237–247 (1977), with the modification that Zwittergent 3-14 detergent (available from Calbiochem-Behring, La Jolla, Calif. 92037, USA) was used (1% w/v final concentration) to disrupt the vaccines before testing.

Antibody responses were measured by haemagglutination-inhibition (HI) tests. In the HI test, the virus binds antibodies which block the haemagglutination reaction. The lowest concentration of antibodies which will block the reaction is taken as a measure of the antigenicity of the virus. The antibodies used were those raised from the same strains of virus, i.e. 157M, 157G and 157E. In Table 1, which shows the results as an average for each group of four animals, the higher the value (which is the reciprocal of the dilution concentration), the greater the antibody response. The homologous responses are underlined.

TABLE 1

Immunisation of guinea pigs with MDCK or egg grown A/Christ/157/83(H1N1) influenza vaccines

| Candidate vaccine strain | HI response of antibodies from the following viruses | | |
|---|---|---|---|
| | 157M ($M_6$) | 157G ($Am_1Al_2$) | 157E ($Al_7$) |
| ($M_6$) | 280 | 150 | 20 |
| ($Am_1Al_2$) | 90 | 68 | 105 |
| ($Al_7$) | 20 | 20 | 960 |

Table 1 shows that the egg-like egg-grown 157E vaccine produced a specific immune response to the homologous virus. In contrast, vaccines prepared using the cell-like egg-grown and cell-like cell grown viruses 157G and 157M, respectively, induced more broadly reacting antibody populations.

EXAMPLE 2

This example shows that cell-like, egg-grown viruses can readily be differentiated from egg-like egg-grown viruses using a range of monoclonal antibodies.

Hybridoma cells secreting monoclonal antibodies against various strains of A(H1N1) influenza were prepared by the conventional mouse spleen cell - mouse myeloma fusion method. Cells which secreted monoclonal antibodies to the virus were selected on the basis of their ability to react in an enzyme-labelled solid phase binding assay with purified virus.

The cell-like egg-grown virus 157G from Example 1 which had been isolated in the amniotic cavity and then passaged twice in the allontoic cavity of eggs, designated "157G ($Am_1$ $Al_2$)", was then compared with 157M ($M_3$) and 157E ($Al_3$), in an HI test as described in Example 1, using 63 different monoclonal antibodies. The results are shown in Table 2. Referring to Table 2, it will be seen that particular monoclonal antibodies frequently showed a similarly high titre to 157M and 157G, whereas the titre for 157E was very low. The clearest instances have been asterisked. It will be seen that few of the A/Christ/157/83 strains from the 1983 outbreak reacted well with antibodies from strains of earlier outbreaks. The last two digits in the strain code show the year in which the isolate was made A/USSR/92/77 being a 1977 isolate and so on. A/-Christ/91/83 is another strain from the same 1983 outbreak and here it was easily possible to find monoclonal antibodies which reacted well against the A/-Christ/157/83 strains. In all but two instances, the cell-like character of 157G could be observed by comparison with 157M.

TABLE 2

HI test of monoclonal antibodies for determining cell-like antigenic properties of an egg-grown strain

| Strain from which monoclonal antibody is derived | Monoclonal antibody code number | A/Christ/157/83 reference strains: 157M($M_3$) | 157E($Al_3$) | A/Chr/157/83 candidate strain 157G($Am_1Al_2$) |
|---|---|---|---|---|
| A/USSR/92/77 | 22 | < | < | 100 |
| | 70 | < | < | 200 |
| | W18 | 200 | < | 800 |
| A/Brazil/11/78 | 27 | < | < | < |
| | 170 | < | < | < |
| A/Eng/333/80 | 14 | 400 | < | 1600 |
| | 17 | < | < | < |

TABLE 2-continued HI test of monoclonal antibodies for determining cell-like antigenic properties of an egg-grown strain

| Strain from which monoclonal antibody is derived | Monoclonal antibody code number | A/Christ/157/83 reference strains | | A/Chr/157/83 candidate strain |
|---|---|---|---|---|
| | | 157M(M$_3$) | 157E(Al$_3$) | 157G(Am$_1$Al$_2$) |
| | 23 | 400 | < | 3200 |
| | 25* | 400 | < | 600 |
| | 44 | < | < | < |
| | 58 | 800 | 1600 | 2400 |
| | 61* | 1600 | < | 3200 |
| | 85 | < | < | < |
| A/Baylor/5700/82 | 1 | 1600 | 3200 | 2400 |
| | 2 | < | < | < |
| | 7 | 3200 | < | < |
| | 9 | < | < | < |
| | 11 | < | 6400 | < |
| | 16 | < | 6400 | < |
| | 26 | < | < | < |
| | 31 | < | < | < |
| | 34 | < | < | < |
| | 41* | 3200 | < | 3200 |
| | 43 | < | < | < |
| | 45 | < | < | < |
| | 51 | < | < | < |
| | 69 | < | < | < |
| A/Baylor/11515/82 | 1 | 6400 | 9600 | 6400 |
| | 3 | < | < | < |
| | 5* | 9600 | 600 | 9600 |
| | 8 | 1600 | 150 | 800 |
| | 11 | < | 6400 | < |
| | 14 | 12800 | 4800 | 9600 |
| | 15 | 9600 | 3200 | 6400 |
| | 16* | 9600 | 400 | 9600 |
| | 17 | 9600 | 1200 | 9600 |
| | 19 | 6400 | 1600 | 1600 |
| | 22 | 9600 | 6400 | 9600 |
| | 23 | 4800 | 1600 | 1600 |
| | 25 | 9600 | 3200 | 9600 |
| | 26* | 4800 | < | 3200 |
| | 28 | 6400 | 4800 | 4800 |
| | 31 | 6400 | 4800 | 4800 |
| | 32 | < | < | < |
| | 33 | < | < | < |
| | 41 | 12800 | 4800 | 6400 |
| | 43* | 600 | < | 3200 |
| A/Christ/91/83 isolated in animal cells | 336* | >12800 | 1600 | 12800 |
| | 354 | 12800 | 6400 | 9600 |
| | 384 | 3200 | < | 200 |
| | 488* | >12800 | 1200 | 12800 |
| | 720* | 4800 | < | 2400 |
| | 721* | 1200 | < | 1200 |
| | 722* | >12800 | 300 | 12800 |
| | 723* | 4800 | < | 3200 |
| | 724* | 4800 | < | 3200 |
| | 725* | >12800 | < | 12800 |
| | 726* | 4800 | < | 6400 |
| | 736* | 4800 | < | 6400 |
| | 737* | 4800 | < | 1600 |
| | 740* | 12800 | 800 | 9600 |
| | 743* | 4800 | < | 6400 |
| | 747* | 4800 | < | 9600 |

< = less than 100

EXAMPLE 3

This Example illustrates the use of polyclonal ferret sera to distinguish between cell-like and egg-like egg-grown viruses.

In an HI test as described in Example 1, but using ferret sera, the results (see Table 3) show that strain 157G (cell-like, grown in eggs) is similar to 157M (cell-grown) and dissimilar from 157E (egg-like, grown in eggs).

TABLE 3

HI test of ferret polyclonal antisera for determining cell-like antigenic properties of egg-grown viruses

| Ferret antisera | A/Christ/157/83 reference strains | | A/Christ/157/83 candidate strain |
|---|---|---|---|
| | 157M(M$_6$) | 157E(Al$_7$) | 157G(Am$_1$ Al$_2$) |
| Anti-157M | 1280 | 320 | 260 |
| Anti-157E | 120 | 1280 | 120 |

EXAMPLE 4

This Example illustrates the preparation of two reassortant influenza vaccine viruses, the selection of one of them as being cell-like and rejection of the other as being egg-like.

The technique for preparation of the reassortants was essentially simultaneous infection of eggs with parental virus (viz. A/Christ/157/83G or A/Christ/157/83E with relatively low growth in eggs) and either A/PR/8/34 (H1N1) or X-31 (H3N2) virus. Both the latter viruses have high growth capacity in eggs X-31 has 6 genes from A/PR/8/34 virus and can be used as an alternative virus to A/PR/8/34 to donate 'high growth genes'. The high growth parent virus is suppressed with antiserum, allowing the growth of viruses with the required HA or NA proteins of 157G and 157E but also with the high growth capacity of A/PR/8/34 virus. The technique is as follows:

1. Double inoculation into eggs with the H1N1 parent strain (either A/Christ/157G ($Am_1$ $Al_1$) or A/-Christ/157E ($Al_2$), and X-31 virus (available from many laboratories including National •Institute of Biological Standards & Control, Blanche Lane, South Mimms, Potters Bar, Hertford, EN6 3QG. England).

These viral strains ($10^5$ and $10^3$ p.f.u. respectively) were injected into the allantoic cavity of embryonated hens' eggs and the eggs were incubated at 35°-36° C. for 24 hours.

2. The allantoic fluid was extracted from the eggs and was incubated for 1 hour at room temperature with various dilutions of anti HA (X-31) goat serum and anti NA (MRC-11) rabbit serum. These antisera suppress growth of parental X-31 virus. The samples of greatest dilution which survive the incubation and neutralisation should be those most likely to be free of the un-reassorted high-growing virus and were selected for the next step by growth in embryonated hens' eggs for 2-3 days at 35°-36° C. Individual eggs which are positive for the virus at this stage are known in the art as the "terminal clones".
3. The terminal clones were analysed serologically with post-infection ferret anti-HA antisera. Those clones giving the required high yield of haemagglutinin were selected.
4. The clones from step 3 were subjected to a repeat of steps 2 and 3.
5. The clones from step 4 were analysed with rabbit anti-NA antisera to select a clone with a correct neuraminidase. For a fuller description of the procedure, see "Influenza, the Virus and the Disease" by C. H. Stuart-Harris. G. C. Schild and J. S. Oxford, Edward Arnold Ltd. (1985) pages 15 to 17.
6. Infectivity and growth experiments were performed to confirm that the selected clones were high yielding in eggs.
7. Seed virus was produced from SPF eggs (of specific pathogen-free hens) by the above-described terminal dilution method.
8. Surface HA and NA antigens were re-checked using serological tests such as the above-described HI and NI tests with monoclonal and polyclonal antibodies.
9. Production of experimental batches of purified and concentrated NIB-14 ($Am_1$ $Al_6$) and NIB-15 ($Al_{12}$) virus to check growth properties, such as yield of HA, morphology by electron microscopy and sedimentation characteristics in 10-40% w/v sucrose gradients. The virus was purified by differential centrifugation as described in Example 1 under "Tests on guinea pigs." Virus concentrate was resuspended in PBS to a protein concentration of 10 mg/ml and stored in individual vials at −70° C.
10. Protein and RNA gene analysis of reassortants were performed to establish the parental origin of their genes. The methodology for this step is described by J. S. Oxford et al., Vaccine 4, 9-14 (1985).

After step 9 one clone from reassortant NIB-14 derived from 157G (a cell-like egg-grown strain) and egg-like clones from reassortant NIB-15 derived from 157E (an egg-like egg-grown strain) were subjected to the HI test using a panel of monoclonal antibodies. They were compared with the reference strains A/Christ/157/83E and A/Christ/157/83M, herein abbreviated to "157E" (egg-grown) and "157M" (cell-grown). The results are shown in Table 4A. It is seen very clearly that NIB-14 clone 40 is cell-like, having a profile similar to that of 157M, whereas the NIB-15 clones were egg-like. The NIB-14 clone was accordingly selected for use in formulating a vaccine.

Table 4B shows the results of an HI test using polyclonal ferret sera, using the same reference strains as in Table 4A. These results further confirm the cell-like character of "157" and of the reassortants obtained from NIB-14.

Sub-unit vaccines were made from NIB-14 Clone 40 and NIB-15 Clone 59 and tested in hamsters, guinea pigs and mice. The animals tested do not suffer from influenza in their normal life, but are susceptible. Such animals, with no history of influenza, are therefore very useful for test purposes. (A difficulty in testing on humans is that they have normally made antibodies against various strains of influenza virus as a result of their previous susceptibility in normal life).

For the tests on hamsters, guinea pigs and mice, the sub-unit vaccines were made by the procedure of M. I. Brady and I. G. S. Furminger, Journal of Hygiene 77, 161-172 (1976). For hamsters and guinea pigs, beta-propiolactone was used as the inactivating agent, while for mice the same formalin inactivation procedure was used as for guinea pigs in Example 1. The animals were vaccinated intramuscularly or intraperitoneally and post-vaccination sera collected and tested for antibodies by HI test against virus (the same NIB-14 or NIB-15). The viruses used in the HI test were standardised to amounts equivalent to 8 agglutinating doses of haemagglutinin. Tables 4C, 4D and 4E show the results and are annotated with further details of the test procedure. In every case the antibody response to the homologous virus was markedly stronger than to the heterologous virus.

TABLE 4A

HI test of monoclonal antibodies for cell-like antigenic properties of four candidate reassortant strains.

| Monoclonal antibody code number | A/Christ/157/83 reference strains | | NIB-14 Clone 40 | A/Chr/157/83 reassortants candidate strains | |
|---|---|---|---|---|---|
| | 157M(M$_6$) | 157E(Al$_7$) | (Am$_1$Al$_6$) | NIB-15 Clone 23 (Al$_{12}$) | NIB-15 Clone 59 (Al$_{12}$) |
| 336$^{ch}$ | 25600 | 800 | 25600 | 1600 | 800 |
| 14$^e$ | 800 | < | 1600 | < | < |
| 23$^e$ | 1200 | < | 3200 | < | < |
| 25$^e$ | 400 | < | 600 | < | < |
| 61$^e$ | 4800 | < | 9600 | < | < |
| 1$^{ba}$ | 1200 | 4800 | 800 | 3200 | 2400 |
| 3$^{ba}$ | < | 25600 | < | 25600 | 25600 |
| 7$^{ba}$ | 19200 | 600 | 6400 | 2400 | 25600 |
| 11$^{ba}$ | < | 25000 | < | 3200 | 25600 |

< = less than 200
$^{ch}$A/Christ/91/83 isolated in MDCK cells
$^{ba}$A/Baylor/5700/82 (H1N1)
$^e$A/Eng/333/80 (H1N1)

TABLE 4B

HI test of ferret polyclonal antisera for a cell-like egg-grown strain and for cell-like antigenic properties of two candidate reassortant strains

| Ferret antisera | A/Christ/157/83 reference strains | | A/Christ/157/83 candidate strains | | |
|---|---|---|---|---|---|
| | 157M (M$_6$) | 157E (Al$_7$) | 157G (Am$_1$Al$_2$) | NIB-14 Clone 40 (Am$_1$Al$_6$) | NIB-15 Clone 59 (Al$_{12}$) |
| Egg-grown virus | | | | | |
| 5/84 | 50 | 800 | 75 | 50 | 1200 |
| 6/84 | 75 | 800 | 75 | 75 | 800 |
| 7/84 | 100 | 1200 | 100 | 75 | 1600 |
| 5/85 | 100 | 6400 | 100 | 100 | 6400 |
| 7/85 | 200 | 6400 | 300 | 200 | 6400 |
| 37/85 | 100 | 4800 | 75 | 75 | 3200 |
| 38/85 | 200 | 3200 | 300 | 150 | 4800 |
| 30/85 | 300 | 6400 | 300 | 200 | 6400 |
| 40/85 | 200 | 4800 | 200 | 150 | 4800 |
| 50/86 | 200 | 3200 | 150 | 150 | 4800 |
| 51/86 | 300 | 6400 | 300 | 300 | 6400 |
| MDCK grown virus | | | | | |
| 10/84 | 600 | 100 | 400 | 400 | 300 |
| 1/85 | 4800 | 400 | 1600 | 4800 | 600 |
| 2/85 | 1600 | 200 | 800 | 1200 | 400 |
| 3/85 | 2400 | 400 | 1200 | 2400 | 600 |
| 27/85 | 1600 | 300 | 800 | 1200 | 400 |
| 28/86 | 1200 | 300 | 800 | 1200 | 400 |
| 7/86 | 1200 | 300 | 800 | 800 | 300 |
| 48/86 | 1600 | 200 | 800 | 1200 | 600 |
| 49/86 | 1600 | 300 | 800 | 1200 | 400 |

TABLE 4C

Antibody response of hamsters to vaccination with sub-unit vaccine

| Vaccine | No. Hamsters | Post-vaccine antibody response (HI test) | | | |
|---|---|---|---|---|---|
| | | Geometric mean titres | | Significant Rises (%) | |
| | | NIB-14 | NIB-15 | NIB-14 | NIB-15 |
| NIB-14 | 20 | 29 | <10 | 55 | 20 |
| NIB-15 | 20 | <10 | 55 | 5 | 55 |

Notes to Table 4C:
Two groups of 20 animals were vaccinated intramuscularly with 2 doses of 10 μg HA/0.5 ml., 14 days apart. The animals were bled 14 days after the second dose. Results are expressed as the geometric mean. The number of significant rises, defined as from a pre-vaccination titre of less than 10 to a post vaccination titre of 40 or higher, in individual animals was determined and expressed as a percentage of the number of animals tested.

TABLE 4D

Antibody response of guinea pigs to vaccination with sub-unit vaccine

| Vaccine | Post-vaccine antibody response HI response | |
|---|---|---|
| | NIB-14 | NIB-15 |
| NIB-14 | 320 | 120 |
| | 80 | 40 |
| | 40 | 20 |
| | 40 | <20 |
| NIB-15 | <20 | 80 |
| | 40 | 640 |
| | <20 | 320 |
| | 40 | 240 |

Notes to Table 4D:
Two groups of four animals were vaccinated intramuscularly with one dose of 16 μg HA/0.5 ml. followed by a further dose of 4 μg HA/0.5 ml. 14 days later. The animals were bled 7 days after the second dose.

TABLE 4E

Antibody responses of mice to vaccination with sub-unit vaccine

| Vacine | Post-vaccine antibody response (HI test) | | | |
|---|---|---|---|---|
| | BABL 1c mice | | CBA mice | |
| | NIB-14 | NIB-15 | NIB-14 | NIB-15 |
| NIB-14 | 240 | <20 | 40 | <20 |
| | 240 | <20 | 60 | <20 |
| | 320 | 20 | 240 | 60 |
| | 60 | <20 | 480 | 20 |
| | 60 | <20 | 240 | <20 |
| NIB-15 | <20 | 960 | <20 | >2560 |
| | <20 | 1920 | <20 | 2560 |
| | <20 | 2560 | <20 | >2560 |
| | <20 | >2560 | 40 | 2560 |
| | <20 | 2560 | 80 | 2560 |

Notes to Table 4E:
Groups of five animals were vaccinated intraperitoneally with a single dose of 30 μg HA in Freund's complete adjuvant. The animals were bled 23 days later.

EXAMPLE 5

This Example illustrates that egg-grown influenza viruses of type B are also selectable on the basis of having cell-like antigenic characteristics It also illustrates the use of an egg-like reference strain isolated in MDCK cells, but having egg-like character conferred on it by one passage in eggs.

The candidate strains in this Example were obtained from a volunteer patient who was deliberately infected with a strain of influenza of type B at the Medical Research Council's Common Cold Unit, Salisbury, England. The patient was infected with a strain B/Christ/112/82 isolated at Christ's Hospital School, supra in 1982. Nasal wash from a volunteer infected with this strain was isolated in eggs and passaged once in eggs ($Al_2$) to provide a strain designated "4465" and the same nasal wash was re-isolated in human embryo trachea cells and passaged once in eggs ($HET_1 Al_1$) to provide a strain designated "4468". These strains were compared in an HI test with reference strains, designated B/EFR/83, obtained from the same nasal wash. These reference strains were derived from virus isolated in MDCK cells. One was passaged further in MDCK cells ($M_2$) and the other was passaged further in the allantoic cavity of embryonated hens eggs ($M_1 Al_1$). The results are shown in Table 5 below. It will be seen from Table 5 that 4465 has cell-like characteristics whereas 4468 was egg-like. 4465 was accordingly selected for use in a vaccine.

TABLE 5

HI test of monoclonal antibodies for determining cell-like antigenic properties of two candidate wild type strains

| Strain from which monoclonal antibody is derived | Monoclonal antibody code number | B/EFR/83 Reference strains | | Candidate strains | |
|---|---|---|---|---|---|
| | | ($M_2$) | ($M_1Al_1$) | 4465 ($Al_2$) | 4468 ($HET_1Al_1$) |
| B/Oregon/5/80 (egg-grown) | 21 | < | 6400 | < | 12800 |
| | 124 | < | < | 200 | 600 |
| | 146 | < | 800 | < | < |
| | 195 | 9600 | 4800 | >25600 | >25600 |
| | 238 | < | 4800 | < | >12800 |
| | 680 | 150 | 800 | 200 | >12800 |
| | 682 | < | 800 | < | < |
| | 710 | < | 800 | < | >12800 |
| B/Chr/145/82 (MDCK cell grown) | 209/385 | 150 | < | 300 | 150 |
| B/Chr/222/82 (MDCK cell grown) | 806 | 9600 | 3200 | 12800 | 4800 |

< = less than 20

We claim:

1. A process of selecting a strain of an influenza virus for use in formulating a vaccine, which process comprises the steps of:
   isolating candidate influenza virus strains, taken from sources of infection, in embryonated hens' eggs;
   determining immunologically whether they have antigenic similarities to animal cell-grown reference strains which are the same as said candidate strains except that they have been isolated and grown exclusively in animal cells; and
   selecting for the vaccine at least one such antigenically similar (cell-like) candidate strain or a reassortant thereof having the HA (hemagglutinin) and NA (neurominidase) genes of said cell-like candidate strain of influenza virus;
   said antigenic similarities being defined by reaction of said candidate strain in a haemagglutination-inhibition test with a panel of at least two different antibodies to the haemagglutinin protein of influenza virus, which are capable of differentiating between a first reference strain which is identical to said candidate strain, but which is isolated and grown exclusively in animal cells and a second reference strain identical to the candidate strain but isolated and grown exclusively in eggs, wherein said reaction of said candidate strain with each antibody of said panel is more similar to that of said first reference strain than to that of said second reference strain.

2. A process according to claim 1, wherein antibodies are provided as sera from animals which have an immune response to the influenza virus, or as monoclonal antibodies.

3. A process according to claim 2, wherein ferret sera are used.

4. A process according to claim 1, wherein the influenza virus is human influenza virus of type A (H1N1) or B.

5. A process of preparing an inactivated vaccine against influenza, which process comprises the steps of:
   isolating candidate influenza virus strains, taken from sources of infection, in embryonated hens' eggs;
   determining immunologically whether they have antigenic similarities to cell-grown reference strains which are the same as said candidate strains except that they have been isolated and grown exclusively in animal cells;
   selecting for the vaccine at least one such antigenically similar (cell-like) candidate strain or a reassortant thereof having the HA and NA genes of said cell-like candidate strain of influenza virus;
   growing said selected strain in embryonated eggs; and
   inactivating particles of the virus to produce inactivated particles;
   said antigenic similarities being defined by reaction of said candidate strain in a haemagglutination-inhibition test with a panel of at least two different antibodies to the haemagglutinin protein of influenza virus, which are capable of differentiating between a first reference strain which is identical to said candidate strain, but which is isolated and grown exclusively in animal cells and a second reference strain identical to said candidate strain but isolated and grown exclusively in eggs, wherein said reaction of said candidate strain with each antibody of said panel is more similar to that of said first reference strain than to that of said second reference strain.

6. A process according to claim 5, which further comprises either disrupting said inactivated particles to prepare a split vaccine or extracting HA and NA components therefrom to prepare a sub-unit vaccine.

7. A process of preparing a live vaccine against influenza, which process comprises the steps of:

isolating candidate influenza virus strains, taken from sources of infection, in embryonated hens' eggs;

determining immunologically whether they have antigenic similarities to animal cell-grown reference strains which are the same as said candidate strains except that they have been isolated and grown exclusively in animal cells;

selecting for the vaccine at least one such antigenically similar (cell-like) candidate strain; and preparing a reassortant thereof having the HA and NA genes of said cell-like candidate strain of influenza virus, in which it is attenuated;

said antigenic similarities being defined by reaction of said candidate strain in a haemagglutination-inhibition test with a panel of at least two different antibodies to the haemagglutinin protein of influenza virus, which are capable of differentiating between a first reference strain which is identical to said candidate strain, but which is isolated and grown exclusively in animal cells and a second reference strain identical to said candidate strain but isolated and grown exclusively in eggs, wherein said reaction of said candidate strain with each antibody of said panel is more similar to that of said first reference strain than to that of said second reference strain.

* * * * *